(12) United States Patent
Lee et al.

(10) Patent No.: US 7,816,509 B2
(45) Date of Patent: Oct. 19, 2010

(54) **TRANSLATIONAL ELONGATION FACTOR PROMOTER FROM *PICHIA PASTORIS* AND METHOD FOR PRODUCING RECOMBINANT PROTEIN USING THE SAME**

(75) Inventors: Hong Weon Lee, Daejeon (KR); Jung Oh Ahn, Daejeon (KR); Joon Ki Jung, Daejeon (KR); Eui Sung Choi, Daejeon (KR); Chun Suk Kim, Daejeon (KR); Eun Gyo Lee, Daejon (KR); Ji Yeon Hong, Daejeon (KR); Hyeok Won Lee, Daejeon (KR); Myoung Soo Park, Daejeon (KR)

(73) Assignee: Korean Research Institute of Bioscience & Biotechnology, Daejeon (KR)

( * ) Notice: Subject to any disclaimer, the term of this patent is extended or adjusted under 35 U.S.C. 154(b) by 127 days.

(21) Appl. No.: 12/094,138

(22) PCT Filed: Jan. 19, 2006

(86) PCT No.: PCT/KR2006/000215

§ 371 (c)(1),
(2), (4) Date: Aug. 19, 2008

(87) PCT Pub. No.: WO2007/058407

PCT Pub. Date: May 24, 2007

(65) Prior Publication Data

US 2009/0298122 A1 Dec. 3, 2009

(30) Foreign Application Priority Data

Nov. 16, 2005 (KR) ........................ 10-2005-0109697

(51) Int. Cl.
*C07H 21/04* (2006.01)
*C12N 15/63* (2006.01)
*C12N 1/19* (2006.01)

(52) U.S. Cl. ................ 536/24.1; 435/320.1; 435/254.2; 435/325

(58) Field of Classification Search ........................ None
See application file for complete search history.

(56) References Cited

U.S. PATENT DOCUMENTS

| 5,612,198 | A | 3/1997 | Brierley et al. |
| 5,650,294 | A | 7/1997 | Kurth et al. |
| 6,011,147 | A | 1/2000 | Nakari et al. |
| 6,265,185 | B1 | 7/2001 | Muller et al. |

OTHER PUBLICATIONS

CL 489166, disclosed in reference Sessions et al. Plant Cell, 2002. vol. 14, No. 12, pp. 2985-2994.*
Muller, Yeast, vol. 14, Issue 14, pp. 1267-1283, John Wiley & Sons, Ltd., Published Online Dec. 4, 1998.
International Search Report for PCT/KR2006/000215, mailed Aug. 10, 2006.
Written Opinion of the International Searching Authority for PCT/KR2006/000215, mailed Aug. 10, 2006.

* cited by examiner

*Primary Examiner*—Celine X Qian
(74) *Attorney, Agent, or Firm*—Holme Roberts & Owen LLP

(57) ABSTRACT

Disclosed are a *Pichia pastoris*-derived translation elongation factor (TEF) promoter, a recombinant expression vector carrying the promoter and a heterologous protein encoding base sequence operably linked to the promoter, and a host cell transfected or transformed with the recombinant expression vector. Also, a method is provided for producing a heterologous protein. The method comprises culturing the host cell to express the *Pichia pastoris*-derived TEF promoter and isolating the promoter from the culture. The TEF promoter can be utilized for the mass production of heterologous proteins without the need for inducers.

8 Claims, 10 Drawing Sheets

FIG. 1

Degenerated Primer 1

T(G/A)AT T(C)TT A(G)TA T(G/A/C)AC A(G)TC T(C)TG

|  | 40 | | 300 |
|---|---|---|---|
| TEF1_SC | RTEKFEKEAAE | ............................ | VKSVEMHHEQLE |
| TEF1_CA | RTEKFEKEAAE | ............................ | VKSVEMHHEQLA |
| TEF1_YL | RTEKFEKEADE | ............................ | VKSVEMHHEILP |
| TEF1_SSC | RTEKFEKEAAE | ............................ | VKSVEMHHESLD |
| TEF1_AO | RTEKFEKEAAE | ............................ | VKSVEMHHQQLQ |

Degenerated Primer 2

T(C)TC A(G)TG A(G)TG CAT T(C)TC T(G/A/C)AC

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gagaagtttg aaaaagaggc                                              20

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
ctcgtggtgc atctcgac                                                18

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
gattgagcca tcttccaa                                                18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gtactttgga gtctcgaa                                                18
```

```
<210> SEQ ID NO 5
<211> LENGTH: 1380
<212> TYPE: DNA
<213> ORGANISM: Pichia pastoris

<400> SEQUENCE: 5
atgggtaagg aaaagttgca cgttaacgtc gttgttattg acacgtcga tgctggtaaa      60
tctaccacca ccggtcactt gatctacaag tgtggtggta ttgacaagcg taccatcgag     120
aagtttgaaa aagaggctga agagctcggt aagggatctt caagtacgc ctgggttttg     180
gacaagctta aggctgagag agagagaggt atcaccatcg acatcgcttt gtggaagttc     240
gagactccaa agtaccacgt taccgtcatt gacgctccag gtcacagaga tttcattaag     300
aacatgatta ccggtacttc ccaagccgac tgtgccattt tggtcattgc ttccagtatt     360
ggtgagttcg aggctggtat ctccaaggat ggtcaaacca gagagcacgc tcttttggct     420
ttcacctgg gtgtcaagca attgattgtt gccatcaaca gatggactc cgtcaaatgg      480
tctcaaaaga gatacgagga gattgtcaag gaaacttcca acttcatcaa gaaggttggt     540
tacaacccta agactgtccc attcgtccca atttccggat ggaacggtga acacatgatt    600
gagccatctt ccaactgtga ctggtacaag ggatgggaga aggagaccaa ggctggtggt    660
gctaccaagg gtaagacctt gttggaggct attgactcca ttgacccacc atccagacca    720
actgacaagc ctctgagatt gccttttgcag gatgtctaca agattggtgg tatcggaact    780
gtgccagtcg gtagagttga accggtgtc atcaaggctg gtatggtcgt cactttcgcc     840
ccagctggtg tcactaccga agtcaagtcg gtcgagatgc accacgagca attggagcaa    900
ggtgtcccag gtgacaacgt tggattcaac gtcaagaacg tttccgtcaa ggaaatcaga    960
agaggtaacg tctgtggtga ctccaagaac gacccaccaa aggccgctga atctttcaac    1020
gcccaggtca ttatcttgaa ccacccaggt caaatctctg ctggttacgc tccagttttg    1080
gactgtcaca ccgctcacat tgcttgtaag ttcgacgagt tgattgagaa gattgacaga    1140
agaaccggta agaagactga ggagaacccct aagttcatca gtccggtga cgccgctatc    1200
gtcaagttgg tccatctcaa gccaatgtgt gttgaggcct tcactgacta cccacccttta   1260
ggaagattcg ctgtcagaga catgagaaca aatgttgctg tcggtgttat caagtccgtt    1320
gtcaagactg acaaggctgg taaggtcacc aaggctgctc aaaaggccgc taagaaatag    1380

<210> SEQ ID NO 6
<211> LENGTH: 424
<212> TYPE: DNA
<213> ORGANISM: Pichia pastoris

<400> SEQUENCE: 6
ataactgtcg cctctttat ctgccgcact gcatgaggtg tccccttagt gggaaagagt       60
actgagccaa ccctggagga cagcaaggga aaaatacta caacttgctt cataatggtc     120
gtaaaaacaa tccttgtcgg atataagtgt tgtagactgt cccttatcct ctgcgatgtt    180
cttcctctca agtttgcga tttctctcta tcagaattgc catcaagaga ctcaggacta    240
atttcgcagt cccacacgca ctcgtacatg attggctgaa atttccctaa agaatttttt    300
tttcacgaaa atttttttt tacacaagat tttcagcaga tataaaatgg agagcaggac    360
ctccgctgtg actcttcttt tttttcttt attctcacta catacatttt agttattcgc    420
caac                                                                 424

<210> SEQ ID NO 7
```

```
<211> LENGTH: 27
<212> TYPE: DNA
<213> ORGANISM: Artificial Sequence
<220> FEATURE:
<223> OTHER INFORMATION: primer

<400> SEQUENCE: 7
gcagaattca tgatggtcgc gtggtgg                                        27

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
gcagcggccg caagctttta aggccgcaaa ctcgc                               35

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gcaagatcta taactgtcgc ctcttttatc                                     30

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
gcagaattcg ttggcgaata actaaaa                                        27

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
gcaagatctg gatccttttt tgtag                                          25

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
aagaattctt gatagttgtt caattg                                         26
```

TRANSLATIONAL ELONGATION FACTOR PROMOTER FROM *PICHIA PASTORIS* AND METHOD FOR PRODUCING RECOMBINANT PROTEIN USING THE SAME

CROSS-REFERENCE TO RELATED APPLICATIONS

This is the U.S. national phase under 35 U.S.C. §371 of International Application PCT/KR2006/00215, filed Jan. 19, 2006, which claims priority to Korean Patent Application No. 10-2005-0109697, filed Nov. 16, 2005, both of which are expressly incorporated herein by reference.

TECHNICAL FIELD

The present invention relates to a translational elongation factor promoter derived from *Pichia pastoris* and a method for producing recombinant proteins using the same. More particularly, the present invention relates to a TEF promoter derived from *Pichia pastoris*, a recombinant expression vector comprising the TEF promoter and a heterologous protein encoding base sequence operably linked to the promoter, and a host cell transfected or transformed with the recombinant expression vector. Also, the present invention provides a method for producing a heterologous protein, comprising culturing the host cell to express the heterologous protein and isolating the heterologous protein.

BACKGROUND ART

Protein synthesis is a multi-step process that begins with transcription, in which the genetic information encoded by DNA is transferred to an mRNA template. Transcription starts with the process of initiation. RNA polymerase binds to a specific region of DNA, called the promoter, which is usually located upstream of the gene to be transcribed. Many promoters, but by no means all, contain a common (conserved) sequence, called a consensus sequence.

In prokaryotes, the promoter consists of two short sequences at positions −10 and −35 upstream of the transcription start site. The sequence at −10 usually consists of the six nucleotides "TATAAT" (RATA box). The other sequence at −35 usually consists of the six nucleotides TTGACA. Most promoters differ from one another in the actual base sequence and distance from the transcription start site of the consensus sequence. This variability is believed to lead to different frequencies with which promoters initiate the transcription, that is, promoter strengths. The promoter is thus one of the important factors that determines the efficiency of protein production, and extensive research is being conducted to develop strong and specific promoters in various microorganisms.

In this regard, much attention has been paid to *Pichia pastoris* not only because it can be a methylotrophic yeast model useful for the study of methanol metabolism and peroxisome production, but also because it is a host system superior in protein mass production to the conventional yeast *Saccharomyces cerevisiae*. In addition, *Pichia pastoris* is now recognized as one of the industrial resources useful for environmentally friendly bioprocesses thanks to its characteristic metabolism and physiological activity.

*Pichia pastoris* is capable of metabolizing methanol via formaldehyde and then formate into carbon dioxide, which are catalyzed by alcohol oxidase (AOX), formaldehyde dehydrogenase (FLD), and formate dehydrogenase (FMDH), respectively. *Pichia pastoris* has two AOX genes (AOX1 and AOX2 genes). The AOX1 promoter for regulating the AOX1 gene is potent enough to express heterogeneous proteins at a high level in methylotrophic yeasts, whereas the AOX2 promoter (U.S. Pat. No. 5,032,516) is known to be relatively inactive (J. Tschopp et al. Nucleic Acids Res. 1987, vol. 15, pp. 3859-3876). A promoter for the FLD gene has also been developed (D. Resina et al. Journal of Biotechnology, 2004, vol. 109, pp. 103-113). A glyceraldehyde-3-phosphoric acid (GAP) promoter, known as a potent constitutive promoter involved in glycolysis in various microorganisms, was developed in *Pichia pastoris*, as well (Waterham et al. Gene, 1997, vol. 186, pp. 37-44).

The promoters of the genes implicated in the above-mentioned methanol metabolism are inducible promoters which are induced by methanol but are down regulated by glucose. When promoters for the genes responsible for methanol metabolism are utilized, highly combustible methanol is needed to induce the transcription thereof. Thus, care must be taken to prevent fires, and special measures and inspections are required for plant construction. When methanol is used as the carbon source, *Pichia pastoris* grows at a considerably slow rate, thus requiring a long growth period. Recently, constitutive promoters which can induce the expression of genes of interest without an inducer, like GAP promoter, have been preferably developed.

Translation elongation factor (TEF) 1-α, which is involved in the transport of aminoacyl tRNA to ribosomes during the translation process within cells, is one of the most abundant proteins in eukaryotes (L. Slobin, European Journal Biochemistry, 1980, vol. 110, pp. 555-563). In addition, TEF promoters are known as constitutive promoters and have been used for the expression of exogenous proteins in yeasts, such as *Saccharomyces cerevisiae*, *Ashbya gossypii*, *Aspergillus oryzae* and *Yarrowia lipolytica* (S. Steiner et al. Molecular Gene Genetics, 1994, vol. 242, pp. 263-271; N. Kitamoto, Applied Microbiology and Biotechnology, 1998, vol. 50, pp. 85-92; S. Muller et al. Yeast, 1998, vol. 14, pp. 1267-1283). However, there has been no report of using a TEF promoter in *Pichia pastoris* thus far.

DISCLOSURE OF THE INVENTION

Leading to the present invention, intensive and thorough research into a potent constitutive promoter conducted by the present inventors resulted in the finding that under the control of a *Pichia pastoris*-derived TEF promoter, a heterologous protein operably linked thereto can be expressed at a greater yield than under the control of a GAP promoter, which is known as an excellent constitutive promoter, or under the control of TEF promoters derived from other species.

In accordance with an aspect of the present invention, a promoter consisting of a base sequence having at least 70% homology with the base sequence of SEQ ID NO.: 6 is provided.

In accordance with another aspect of the present invention, there is provided a recombinant expression vector, comprising the said promoter and a base sequence operably linked to the promoter coding for a heterologous protein.

In accordance with a further aspect of the present invention, a host cell transformed or transfected with the recombinant expression vector is provided.

In accordance with still a further aspect of the present invention, a method is provided for producing a heterologous protein, which comprises culturing the host cell to express the heterologous protein, and isolating the heterologous protein.

BRIEF DESCRIPTION OF THE DRAWINGS

FIG. 1 depicts the preparation of degenerated synthetic primers based on the common amino acid sequence of TEF from various microorganisms (TEF1_SC, TEF1_CA, TEF1_YL, TEF1_SSC and TEF1_AO are parts of the TEF amino acid sequences from *Saccharomyces cerevisiae*, *Candida albicans*, *Yarrowia lipolytica*, *Schizosaccharomyces cerevisiae*, and *Aspergillus oryzae*, respectively).

BEST MODE FOR CARRYING OUT THE INVENTION

Figure 2A:
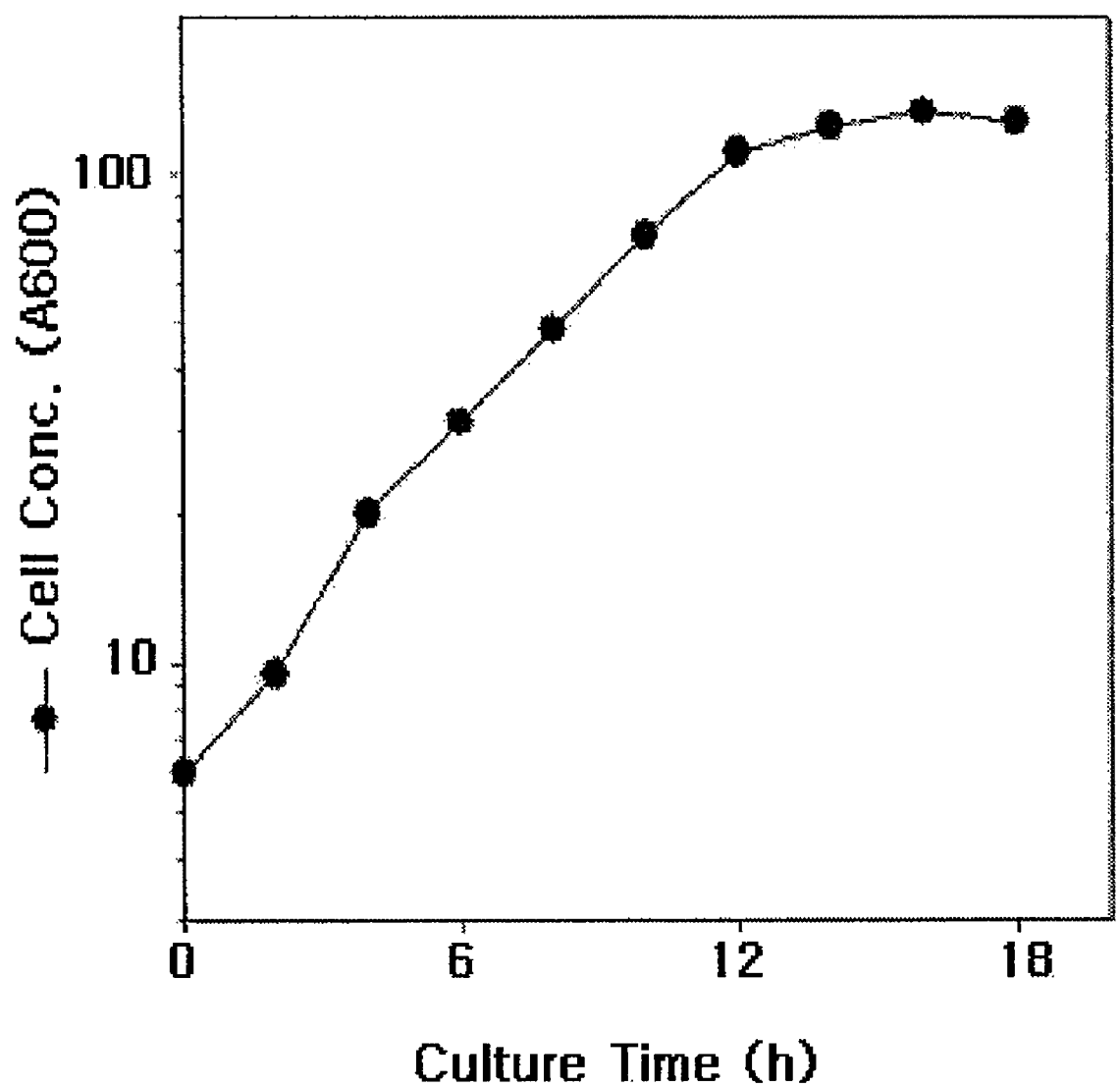
FIG. 2A is a cell growth curve obtained when *Pichia pastoris* is cultured in a batch manner.

It was discovered in the present invention that a gene encoding a translation elongation factor (hereinafter referred to as "TEF") involved in the transport of amino acyl tRNA to ribosomes during the translation process within *Pichia pastoris* is expressed at a high rate in the exponential growth phase but at a low rate in the interphase. This indicates the ability of the TEF gene to be highly expressed with the growth of the strain, even in the absence of an inducer, suggesting that a promoter for the TEF gene derived from *Pichia pastoris* can be used as a constitutive promoter.

The present invention provides a TEF gene derived from *Pichia pastoris*. The TEF gene consists of the base sequence represented by SEQ ID NO.: 5. The TEF gene may be chemically synthesized with reference to the sequence of SEQ ID NO.: 5 or may be prepared through PCR using primers complementary to regions of both ends of SEQ ID NO.: 5, with the genomic DNA of *Pichia pastoris* serving as a template. Having its origin from *Pichia pastoris*, the TEF gene of the present invention can be used as a probe for detecting TEF genes derived from *Pichia* spp.

In addition, the present invention provides a promoter responsible for the expression of the TEF gene. The promoter of the TEF gene consists of the base sequence represented by SEQ ID NO.: 6. Even a part of the base sequence represented by SEQ ID NO.: 6 can function as a promoter for the TEF gene. Accordingly, the present invention also includes a base sequence having at least 70%, preferably 80%, more preferably 90%, and most preferably 95% homology with the base sequence of SEQ ID NO.: 6. The promoter for TEF genes may be chemically synthesized with reference to the sequence of SEQ ID NO.: 6, or may be prepared by PCR using primers complementary to regions of both ends of SEQ ID NO.: 6, with the genomic DNA of *Pichia pastoris* serving as a template. Likewise, having its origin from *Pichia pastoris*, the promoter for TEF genes according to the present invention can be used as a probe for detecting TEF promoters derived from *Pichia* spp. Further, as mentioned above, the "TEF promoter" derived from *Pichia pastoris* according to the present invention can be used as a constitutive promoter.

As used herein, the term "promoter" refers to a regulatory base sequence essential for the expression of a gene, which is usually located upstream of a gene, and to which RNA polymerase binds. As a rule, promoters are divided into two classes. One is an "inducible promoter", which would be operated in the presence of an inducer so as to express a gene under the regulation thereof. In order to utilize such an inducible promoter, an inducer, which is usually expensive, is required. Also, under certain conditions, inducers may be apt to induce toxicity in the body or host cells. In addition, many considerations, such as the time point of inducer addition, inducer concentration, etc., must be taken into account when using inducers during culture. Conversely, a "constitutive promoter" can promote the transcription of a gene under the control thereof even in the absence of an inducer. Thus, constitutive promoters can overcome the problems with using inducible promoters.

To determine the extent to which the TEF promoter of the present invention affects the gene under the control thereof, the expression of the TEF gene is analyzed quantitatively. In an embodiment, the mRNA of the TEF gene is measured for transcription level. The quantitative analysis of the mRNA may be achieved according to a method known in the art. For example, RT-PCR, Northern blotting, dot blot-hybridization, hybridization using DNA array, a DNA microbead method, etc., may be used. In a detailed embodiment, *Pichia pastoris* is cultured, and the total mRNA is isolated from the culture and serves as a template for RT-PCR using primers specific for a TEF gene, so as to synthesize cDNA. Then, Northern blotting is carried out with the cDNA to analyze the expression level of the TEF gene (see Example 2).

The TEF promoter for TEF genes according to the present invention may be in various isoforms because they can function normally even if they share only 70% homology with SEQ ID NO.: 6. It is required that they potently promote the expression of heterogeneous proteins. In accordance with an embodiment of the present invention, a reporter gene is designed to be under the control of the TEF promoter and is analyzed for expression level. Examples of the reporter gene useful in the present invention include lacZ (β-galactosidase), cat (chloramphenicol acetyltransferase), uidA (β-glucuronidase), dhfr (dihydrofolate reductase), neo (neomycin phosphotransferase), aphIV (hygromycin phosphotransferase) or lux (luciferase). In the present invention, it is preferable to use a fusion protein (Ahn et al. Journal of Microbial. Biotechnol. 2003, vol. 13, p. 451) comprising a cellulose-binding domain covalently bonded to *Bacillus stearothermo-*

*philus*-derived lipase. The fusion protein enjoys the advantages of allowing the expression level of the protein of interest to be accurately measured through quantitative analysis of the lipase, secreted with the increased secretion efficiency of the cellulose-binding domain, and also of not inducing toxicity in cells (see Example 3).

Qualitative and quantitative analysis of the expressed reporter protein can be achieved using methods known in the art. For example, antibodies which bind specifically to the reporter proteins or fragments thereof may be used for qualitative and quantitative analysis. Both polyclonal and monoclonal antibodies are useful. Also, the antibodies useful for the analysis include antibodies modified according to known techniques or derivatives thereof, such as Fab fragments, single chain antibodies, etc. For the identification and quantitative analysis of an analyte through antigen-antibody reaction, agglutination assay, enzyme-linked immunosorbent assay (ELISA), Western blotting, focus luminescence assay (FLA), immunoprecipitation, radioimmuoassay (RIA), and/or enzyme immunoassay (EIA), may be conducted for example.

As described above, a gene operably linked to the TEF promoter according to the present invention can be strongly expressed, even in the absence of an inducer, so that the promoter can be used in the production of heterogeneous proteins.

A prerequisite for the production of a heterogeneous protein is the preparation of a recombinant vector comprising a corresponding gene operably linked to the TEF promoter. This recombinant vector constitutes an aspect of the present invention and may be prepared from a well-known or commercially available vector. In this regard, for example, the innate promoter of the vector may be substituted with the TEF promoter according to the present invention. Alternatively, the recombinant vector may be prepared in such a way that it comprises the TEF promoter of the present invention and a regulatory sequence conventionally designed for the vector.

As used herein, the term "vector" means a DNA molecule which serves as a carrier for stably transporting a base sequence coding for a heterogeneous protein into a host cell. To be useful, a vector must be replicable, readily transformable into host cells, and detectable with a suitable means.

The term "recombinant expression vector", as used herein, means a circular DNA molecule containing a heterologous protein-encoding gene which is operably linked thereto so as to be expressed in a host cell. In order to increase the expression level of a gene transfected into a host cell, the gene must be operably linked to transcription and translation regulatory sequences which normally work within the expression host. Preferably, the gene coexists along with a regulatory sequence, a bacteria selectable marker, and a replication origin within one vector.

The term "regulatory sequence", as used herein, indicates a base sequence essential to, or beneficial for, the expression of heterologous proteins. Examples of the regulatory sequence include, but are not limited to, signal sequences, upstream activation sequences, enhancers, polyadenylation sequences, propeptide sequences, and transcription termination factors. The regulatory sequence used in the present invention comprises at least a promoter, and preferably both a promoter and a signal sequence. Optionally, other regulatory sequences may be used, for example, to increase the expression level of a heterologous protein.

Of the regulatory sequences, a "signal sequence" is an amino acid sequence which induces an expressed protein to be transported outside the plasma membrane, thereby making it easy to separate and purify the heterologous protein. Generally, a membrane protein or a secretory protein which is transported into the periplasm space comprises an N-terminal sequence which is to be cut by a signal peptidase. Examples of signal sequences useful in the present invention include α-factor signal sequence, killer toxin leader signal sequence, invertase signal sequence, and α-amylase signal sequence, but are not limited thereto.

When a base sequence coding for a heterologous protein is operably linked to the regulatory sequences including the promoter according to the present invention, the heterologous protein can be expressed in a host cell. By the term "operably linked", as used herein, it is meant that one base sequence is arranged with another in a functional relationship. For example, if a signal sequence participates in secreting a mature protein, it may be said to be operably linked to the protein. The transcriptional control of a promoter over a coding sequence results from operable linking therebetween. A ribosome-binding site is operably linked to a coding sequence when it is present at a position allowing translation of the coding sequence. Generally, by the term "operably linked", it is meant that the linked DNA sequences are in contact with each other; for example, a signal leader is in contact with a gene of interest and exits within a reading frame. When the term "operably linked" is applied to an enhancer, it need not be in contact with a gene or a DNA sequence of interest.

A host cell transformed or transfected with the recombinant expression vector constitutes another aspect of the present invention. The host cells suitable for the present invention may include well-known eukaryotic or prokaryotic host cells such as *E. coli*, *Pseudomonas* spp., *Bacillus* spp., *Streptomyces* spp., fingi, and yeasts, insect cells such as *Spodoptera frugiperda* (SF9), animal cells such as CHO and mouse cells, African green monkey cells such as COS 1, COS 7, BSC 1, BSC 40 and BMT 10, and cultured human cells and plant cells. Preferable is *Pichia pastoris* because it has the same origin as the TEF gene of the present invention.

Transformation or transfection may be conducted according to techniques described in basic experimental literature, such as Davis et al. Basic Methods in Molecular Biology, 1986. Examples of the techniques useful in the present invention include transduction, cationic lipid-mediated transfection, electroporation, DEAE-dextran mediated transfection, calcium phosphate transfection, scrape loading, and infection.

In accordance with another aspect, the present invention provides a method for producing a heterologous protein, comprising culturing the transformed or transfected host cell to express the heterologous protein and isolating the heterologous protein.

Using a well-known technique, the host cell may be cultured in a nutrient medium suitable for the production of heterologous proteins. For instance, cells may be cultured in a laboratory or pilot fermentor on a small or large scale with shaking in the presence of a suitable nutrient medium and allowing a target protein to be expressed and/or isolated. Culturing may be effected in a suitable medium containing a carbon source, a nitrogen source and inorganic salts using a well-known technique. The medium may be commercially available or may be prepared with reference to a catalogue from the American Type Culture Collection. The host cells of the present invention can be cultured in a batch or a fed-batch manner.

"Batch-type culture" is a culturing technique in which all nutrients are added to the medium in an initial fermentation stage. In a batch-type culture, a host cell can proliferate until one of the essential nutrients is exhausted from the medium or until conditions unfavorable for fermentation arise (e.g., the pH of the medium becomes low enough to inhibit the growth of the microorganism).

"Fed-batch culture" is a fermentation technique in which one or more nutrients are continuously fed to a medium just after fermentation is initiated or after the cells have grown to a predetermined phase, or when the nutrients have been exhausted from the medium. For fed-batch culture, the pH of the medium is controlled so as to maintain preferable growth conditions, and supplementation is carried out to prevent the essential nutrients from being exhausted from the medium. The host yeast will continue to grow at a rate depending on the rate of provision of the nutrients. Usually a single nutrient or a carbon source is the growth limiting factor. Other nutrients may also be used as limiting factors. For example, nitrogen, oxygen, vitamins, amino acids, sulfur, and/or phosphorus may be used to restrict the growth of microorganisms when they are auxotrophic therefor.

A heterologous protein of interest can be isolated from the fermented culture using a conventional method exemplified by centrifugation, filtration, extraction, spray drying, evaporation and precipitation. Further, various other methods such as chromatography (for example, ion exchange, affinity, hydrophobic, and size extrusion), electrophoresis, fractional solubility (for example, ammonium sulfate precipitation), SDS-PAGE and extraction may be used for the purification of heterologous proteins.

EXAMPLES

Example 1

Preparation of *Pichia pastoris*-Derived TEF Gene

Degenerated primers (SEQ ID NOS.: 1 and 2) for use in cloning a *Pichia pastoris*-derived TEF gene were designed on the basis of known base sequences of the translation elongation factors of *Saccharomyces cerevisiae, Candida albicans*, and *Schizosaccharomyces cerevisiae* (*Saccharomyces cerevisiae* TEF gene, Genebank No. AAB68129; *Candida albicans* TEF gene, Genebank No. EAK98693; *Schizosaccharomyces cerevisiae* TEF gene, Genebank No. BAA11569), and were synthesized by Geno Tech.

With the genomic DNA of *Pichia pastoris* GS115 serving as a template, PCR was performed using the degenerated primers. The PCR product, determined to have a size of 780 bp, was inserted into a pSTBlue-1 vector (Novagen). The resultant recombinant vector, named pST1, was subjected to base sequencing, which resulted in the finding that the 780 bp DNA fragment shared 92% homology with the TEF1-α gene of *Pichia anomala*. This indicates the 780 bp DNA fragment is a part of the TEF gene of *Pichia pastoris*.

In order to obtain an open reading frame and the promoter of TEF1-α using the 780 bp DNA fragment which served as a probe, inverse PCR was performed with synthesized primers (SEQ ID NOS.: 3 and 4). In this regard, the genomic DNA of *Pichia pastoris*, after being digested with various restriction enzymes, was used as a template. The DNA sequence of interest was detected in the genomic DNA fragment digested with EcoRI as analyzed on gel. The DNA fragment was cloned in a pSTBlue-1 vector. The resultant recombinant vector, named pST2, was subjected to base sequencing to identify an open reading frame of the TEF1-α gene (SEQ ID NO.: 5). Thus, a sequence just upstream of the open reading frame, that is a promoter region (SEQ ID NO.: 6), was obtained as well. The promoter was named $P_{TEF}$.

Example 2

Northern Blotting Analysis of TEF Gene after Batch Type Culture

Because mRNA is synthesized from a gene through transcription, the level of the mRNA can be an indirect indicator of the expression rate of the gene. To determine the level of the mRNA corresponding to the TEF gene, Northern blotting analysis was performed with the TEF gene of Example 1 serving as a probe. In this regard, *Pichia pastoris* was cultured at 30° C. in a medium containing 4% glycerol, 1% yeast extract, and 2% peptone, pH 6.0 (refer to FIG. 2*a*). Samples were taken at predetermined time intervals and the RNA concentration per sample was adjusted to 1.25 µg/ml prior to electrophoresis. The TEF gene of SEQ ID NO.: 5, represented as DIG, was used as a probe.

Figure 2B:
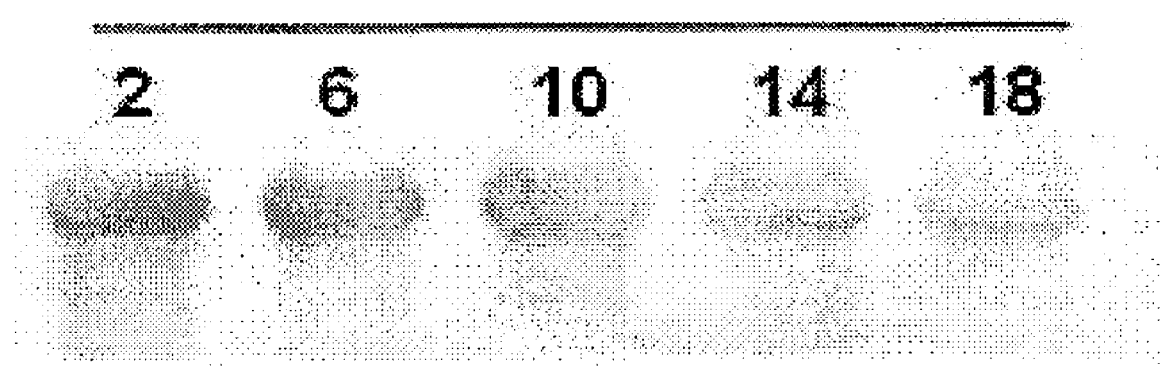
FIG. 2B shows Northern blots of a TEF gene analyzed according to culture time period.

Northern blotting analysis results of the TEF gene are given in FIG. 2*b*. As seen in FIG. 2*b*, TEF was found to be expressed at a high rate in the exponential growth phase of the yeast and at a low rate in the interphase. These results demonstrate the strong expression of the TEF gene even in the absence of an inducer with the growth of the microorganism, suggesting that the TEF promoter can be used as a constitutive promoter.

Example 3

Construction of Recombinant Expression Vector Carrying TEF Promoter

A lipase gene was used as a reporter gene for identifying the activity of the TEF promoter cloned above. To this end, a lipase L1F (CBD-L1-Lipase) in which a cellulose-binding domain (CBD) was connected to the N-terminal of L1 lipase was employed because of its superb ability to stably express lipase L1 (Ahn et al., Journal of Microbial. Biotechnol. 2003, vol. 13, p. 451). A lipase gene expression vector carrying a TEF promoter was constructed from a pPIC9 vector (Invitrogen, U.S. A.).

Figure 3:
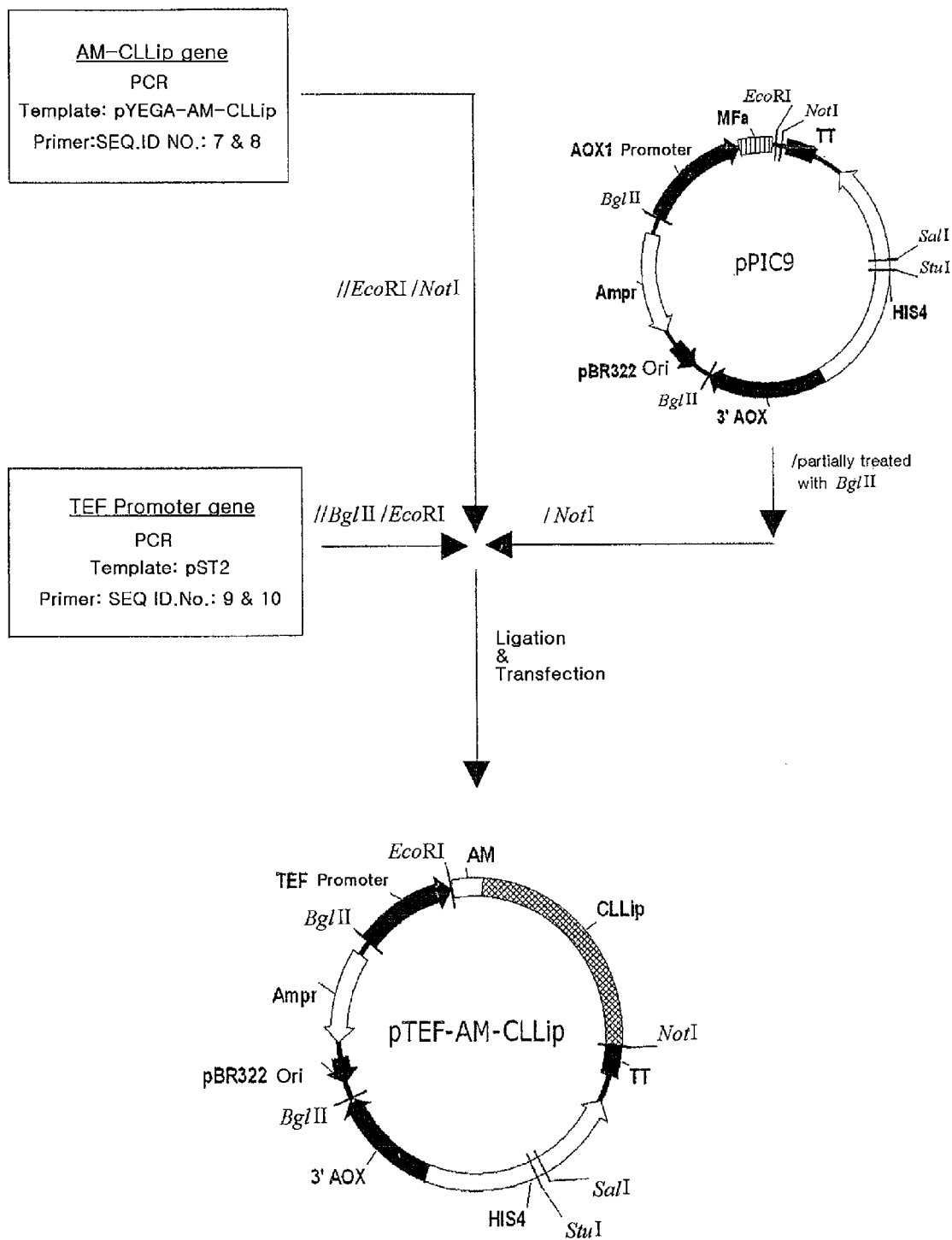
FIG. 3 is a schematic diagram showing the construction of the recombinant expression vector pTEF-AM-CLLip, in which a *Pichia pastoris*-derived TEF promoter is operably linked to a reporter gene.

FIG. 3 shows a recombinant expression vector in which a lipase gene, serving as a reporter gene, is under the control of the TEF promoter. A DNA sequence comprising the signal sequence α-amylase and the lipase was amplified from pYEGA-AM-CLLip (Ahn et al. Journal of Microbial. Biotechnol. 2003, vol. 13, p. 451) through PCR using a pair of synthetic primers of SEQ ID NO.: 7 and SEQ ID NO.: 8 (comprising restriction enzyme sites EcoRI and NotI, respectively). Meanwhile, a TEF promoter region was obtained by PCR using a pair of synthetic primers of SEQ ID NO.: 9 and SEQ ID NO.: 10 (comprising the restriction enzyme sites BglII and EcoRI, respectively). The lipase gene thus obtained was digested with EcoRI and NotI while the promoter $P_{TEF}$ was cut with BglII and EcoRI. Both the truncated lipase gene and the TEF promoter were connected to the pPIC9 vector, partially digested with BglII and NotI. The resultant recombinant expression vector, called "pTEF-AM-CLLip", could express a lipase under the control of the TEF promoter, which was doomed to be secreted outside the membrane due to the α-amylase fused thereto.

Figure 4:
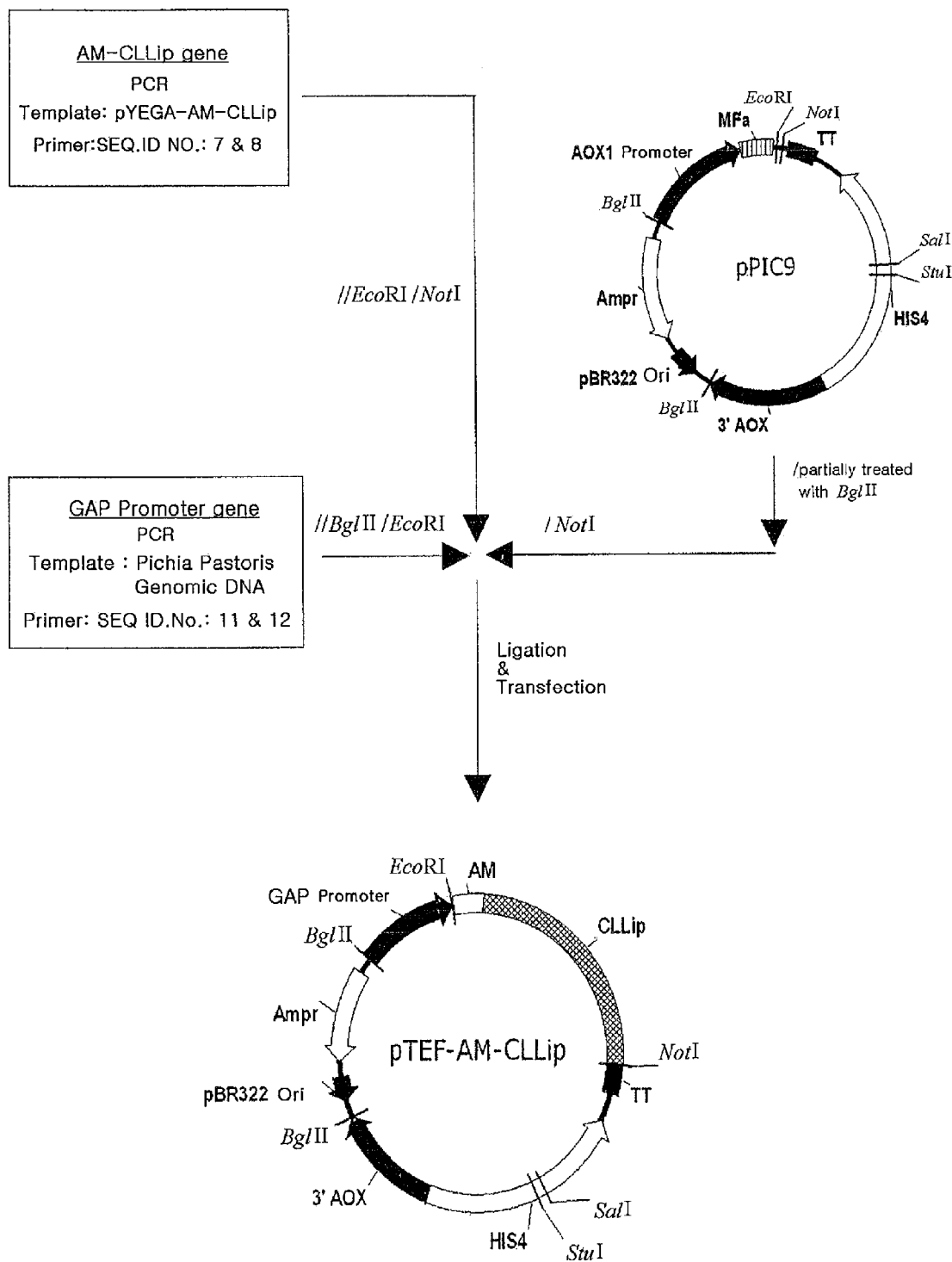
FIG. 4 is a schematic diagram showing the construction of the recombinant expression vector pGAP-AM-CLLip, in which a glyceraldehyde-3-phosphate dehydrogenase (GAP) promoter is operably linked to a reporter gene.
Figure 5A:
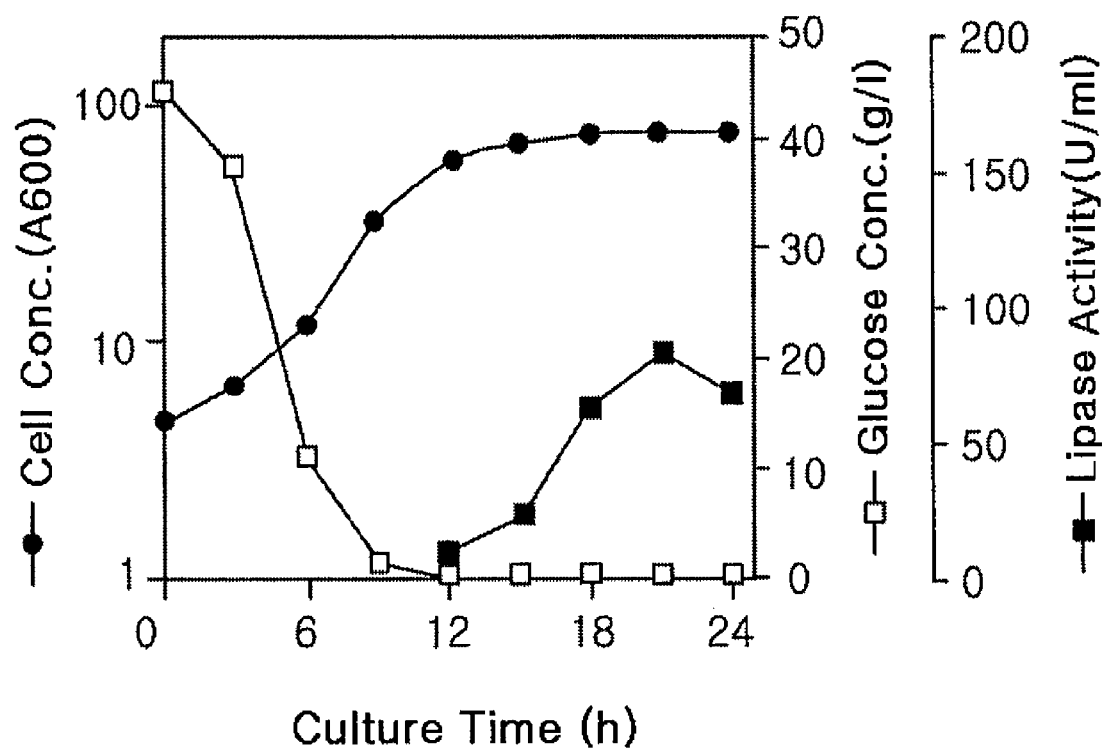
FIG. 5A is a graph obtained after *Pichia pastoris*, transfected with the recombinant expression vector pGAP-AM-CLLip, is cultured in a batch manner using glucose as a carbon source (●: cell concentration, □: glucose concentration, ■: lipase activity).
Figure 5B:
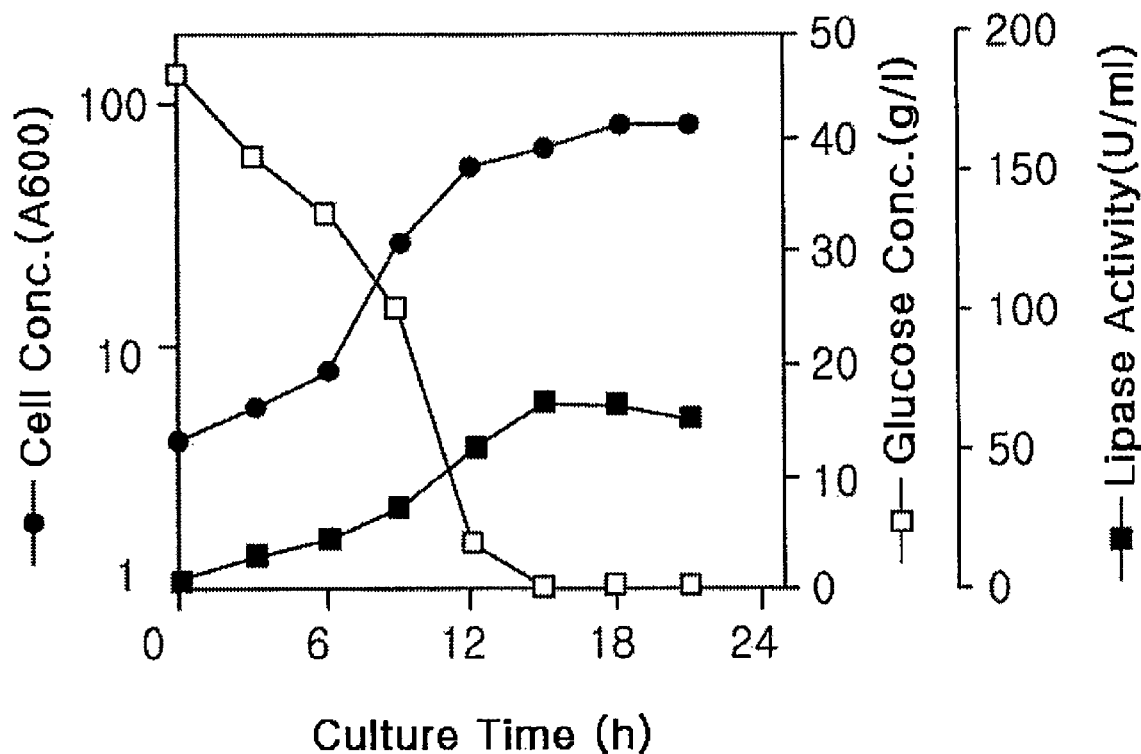
FIG. 5B is a graph obtained after *Pichia pastoris*, transfected with the recombinant expression vector pTEF-AM-CLLip, is cultured in a batch manner using glucose as a carbon source (●: cell concentration, □: glucose concentration, ■: lipase activity).
Figure 5C:
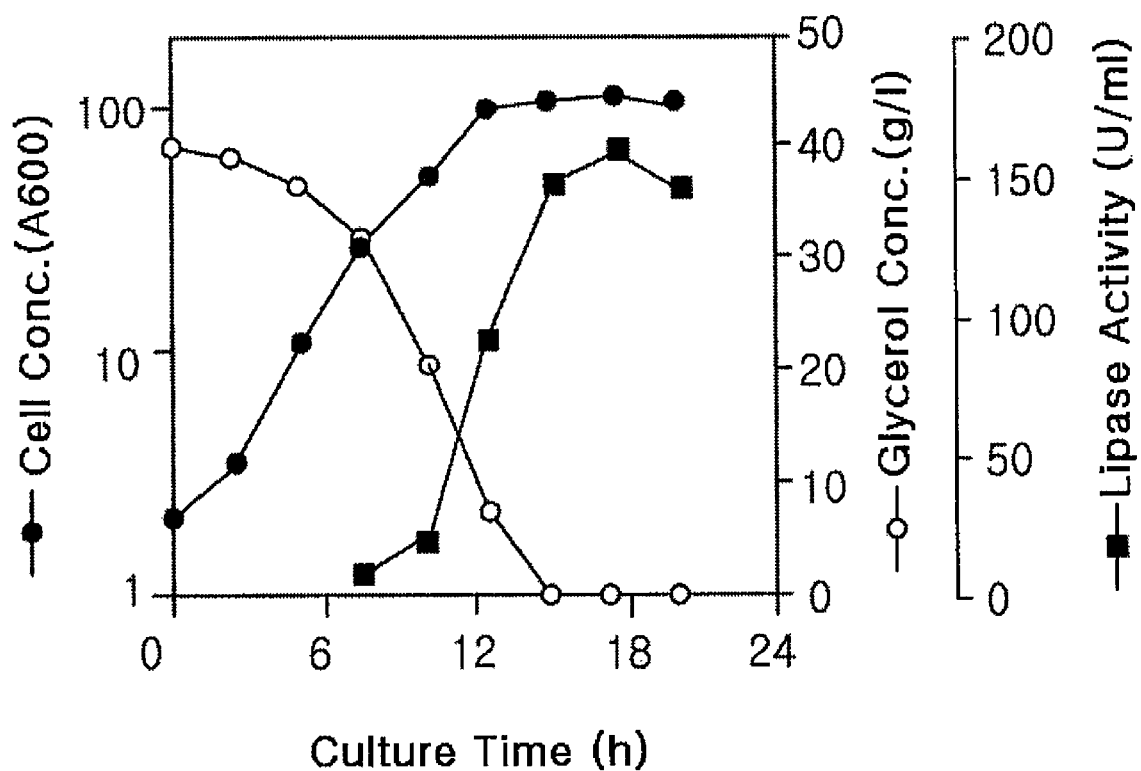
FIG. 5C is a graph obtained after *Pichia pastoris*, transfected with the recombinant expression vector pGAP-AM-CLLip, is cultured in a batch manner using glycerol as a carbon source (●: cell concentration, ○: glycerol concentration, ■: lipase activity).
Figure 5D:
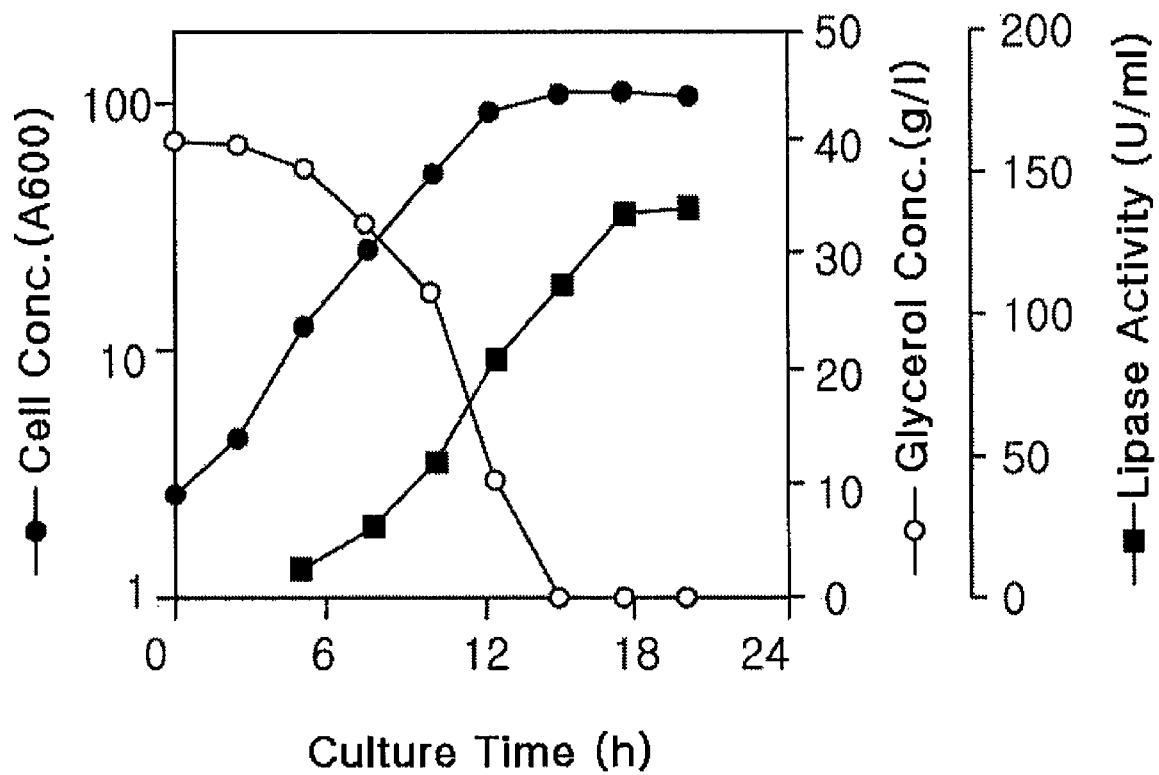
FIG. 5D is a graph obtained after *Pichia pastoris*, transfected with the recombinant expression vector pTEF-AM-CLLip, is cultured in a batch manner using glycerol as a carbon source (●: cell concentration, ○: glycerol concentration, ■: lipase activity).

For comparison with the TEF promoter, a well-known GAP promoter was used as a control. On the basis of the known base sequence, derived from *Pichia pastoris*, the GAP promoter was amplified from the genome of *Pichia pastoris* by PCR using a pair of synthetic primers of SEQ ID NOS.: 11 and 12 (comprising the restriction enzyme sites BglII and EcoRI, respectively). The GAP promoter thus obtained was digested with the restriction enzymes BglII and EcoRI. Both the truncated GAP promoter and the lipase gene treated with EcoRI and NotI were connected to the pPIC9 digested partially with BglII and NotI. The resultant recombinant expression vector, named "pGAP-AM-CLLip", was found to express the lipase under the control of the GAP promoter, which was doomed to be secreted outside the membrane due to the signal sequence α-amylase fed thereto (refer to FIG. 4).

Example 4

Transfection of *Pichia pastoris* pTEF-AM-CLLip and pGAP-AM-CLLip, constructed in Example 3, were individually transfected into *Pichia pastoris* GS115. The transfection was conducted using a lithium/TE method (Hill et al. Nucl. Acids. Res. 1991, vol. 19, p. 5791). In order to individually insert pTEF-AM-CLLip and pGAP-AM-CLLip into the His4 region on the genome of *Pichia pastoris* GS115, the vectors were treated with StuI and transfected into *Pichia pastoris* using the lithium/TE method. In greater detail, the expression vector digested with StuI was mixed with a carrier DNA and PEG/LiAc and left to react at 30° C. for 30 min. Then, DMSO was added before reaction at 42° C. for an additional 15 min. After completion of the reaction, centrifugation was conducted to form a precipitate which was then suspended in 200 μl of a TE solution. The suspension was spread over a His(−) agar plate (glucose 2%, yeast nitrogen source 0.67%, and amino acid mixture lacking histidine 0.077%, agar 2%), followed by incubation for 2-3 days.

Out of the colonies thus formed, transformants which carried a single copy of the recombinant expression vector pTEF-AM-CLLip or pGAP-AM-CLLip on the genome were selected. Through the expression of the lipase, the strength of the TEF promoter could be compared with that of the GAP promoter.

Example 5

Comparison Between TEF Promoter and GAP Promoter Strengths

*Pichia pastoris* transfected with pTEF-AM-CLLip or pGAP-AM-CLLip was cultured in a batch type manner and the level of the lipase expressed during culturing was measured so as to compare TEF promoter strength with GAP promoter strength.

In greater detail, the transformants were cultured in a batch type manner in a medium containing glucose or glycerol 4%, a yeast extract 3%, and peptone 1%. The cell mass was removed from the medium, followed by measurement of the expression level of the lipase.

Also, the cell mass was measured for dried weight, and glucose or glycerol was assayed for level according to culturing time period. Measurement for each parameter was conducted as follows.

(1) Dried cell mass: Cells were obtained by centrifugation, washed with an isotonic solution, and dried at 80° C., and the weight of the dried cell mass was measured.

(2) Lipase Activity Assay: Lipase was assayed for titer using a pH-stat method.

(3) Glucose Assay: Glucose was quantitatively analyzed using a glucose analyzer.

(4) Glycerol Assay: Glycerol was quantitative analyzed using a glycerol analysis kit (Boehringer Mannheim, Germany).

FIGS. 5A to 5D graphically show batch-type culture results of the transformants. In all batch-type cultures, pTEF-AM-CLLip-transfected *Pichia pastoris* and pGAP-AM-CLLip-transfected *Pichia pastoris* exhibited similar cell growth curves with similar expression levels of lipase. In pTEF-AM-CLLip-transfected *Pichia pastoris*, the lipase was expressed in a pattern almost identical to the growth curve, and even at a high concentration of glucose. In contrast, pGAP-AM-CLLip-transfected *Pichia pastoris* allowed the lipase to be expressed from the later stage of the exponential growth phase or at a low concentration of glucose. These data demonstrate that the TEF promoter of the present invention can be used as a constitutive promoter, like the GAP promoter, but is more potent than the GAP promoter because it can express the heterologous protein irrespective of glucose concentration as the cell grows.

Example 6

Comparison Between TEF Promoter and GAP Promoter Strengths in Fed-Batch Type Culture pTEF-AM-CLLip-transfected *Pichia pastoris* and pGAP-AM-CLLip-transfected *Pichia pastoris*, both prepared in Example 4, were cultured in a fed-batch manner in order to compare TEF promoter strength with GAP promoter strength using large populations of cells.

TABLE 1

Compositions of Media Used in Fed-Batch Type Culture

| Composition | Initial Medium (g/l) | Additional Medium (g/l) |
| --- | --- | --- |
| Glucose or Glycerol | 10 | 400 |
| Casein peptone | 40 | 200 |
| Yeast Extract | 10 | 100 |

When the medium was completely depleted of 10 g/l of glucose or glycerol as the transfected *Pichia pastoris* was cultured at 30° C. in the initial medium, pH 5.5, the additional medium started to be fed thereto in such stepwisely increasing amounts from 6 ml/h to 70 ml/l so as to maintain the concentration of glucose and glycerol at 1 g/l or less and the growth rate of cells at 0.03-0.05/h.

Figure 6:
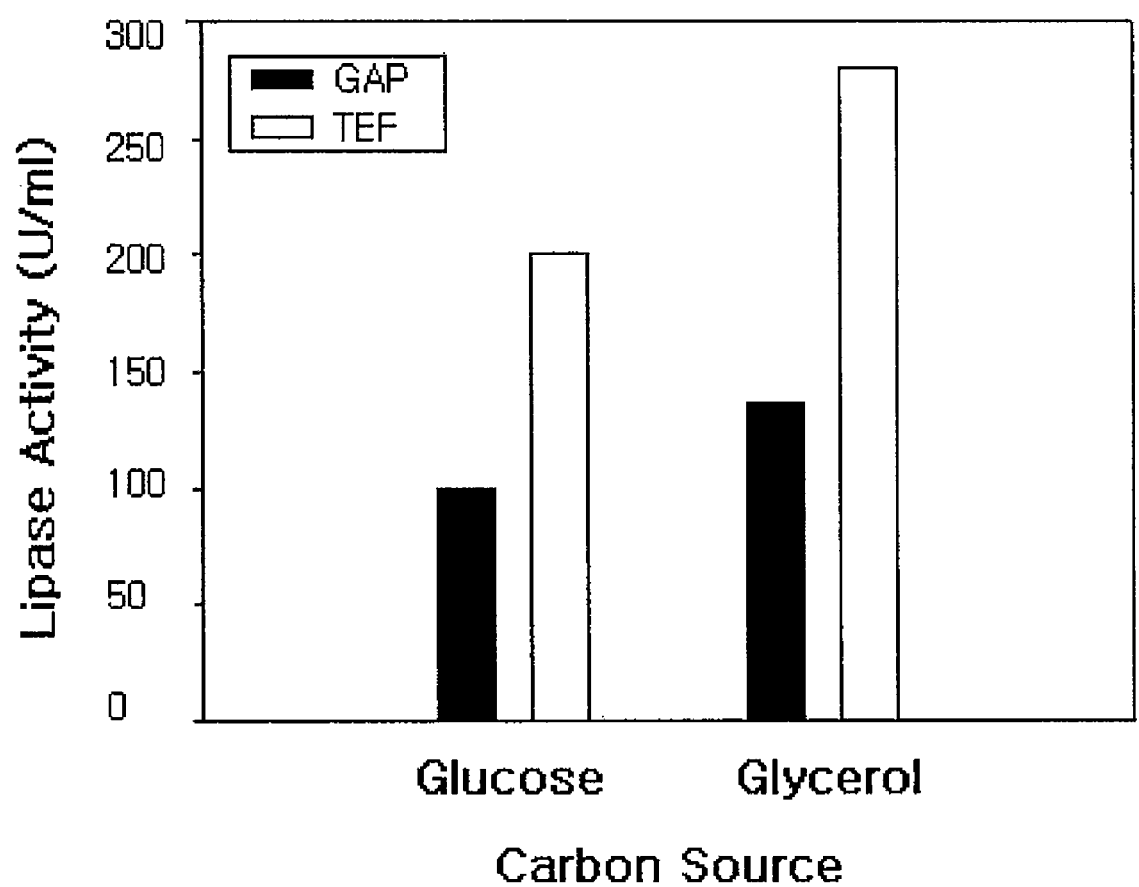
FIG. 6 is a graph showing the comparison of lipase activity between pGAP-AM-CLLi-transfected *Pichia pastoris* and pTEF-AM-CLLip-transfected *Pichia pastoris* alter they are cultured in a fed batch manner (■: lipase activity in pGAP-AM-CLLip-transfected *Pichia pastoris*, □: lipase activity in pTEF-AM-CLLip-transfected *Pichia pastoris*).

The results of the fed-batch type culture, in which glucose or glycerol was used as a carbon source, are given in Table 2, below. For all of the fed-batch type cultures, the carbon source was used as a growth limiting factor and maintained at 1 g/l in the medium. pTEF-AM-CLLip-transfected *Pichia pastoris* and pGAP-AM-CLLip-transfected *Pichia pastoris* were found to exhibit similar growth behaviors, but to greatly differ from each other in lipase expression level, unlike the batch type culture. The expression level of lipase was approximately 1.5 fold greater in pTEF-AM-CLLip-transfected *Pichia pastoris* than in pGAP-AM-CLLip-transfected *Pichia pastoris* (refer to FIG. 6). Although the GAP promoter is known to be a constitutive promoter, account must be taken of cell growth rate, carbon source type, and carbon source concentration during culture in order to overexpress heterologous proteins under the control of the GAP promoter (Gyuseop et al. Biochemical Engineering Journal, 1998, vol. 1, p. 211). However, the lipase expression under the control of the TEF promoter exhibits a behavior pattern similar to the growth behavior of the cell and is believed to increase with the growth of cells.

It is known that the strength of a *Saccharomyces cerevisiae*-derived TEF promoter amounts to only approximately 25% of that of GAP (Mumberg et al. Gene, 1994, vol. 156, p 119). In a fed-batch type culture, the strength of the *Pichia pastoris*-derived TEF promoter according to the present invention is 1.5 times greater than that of GAP. In consequence, the *Pichia pastoris*-derived TEF promoter of the present invention is a constitutive promoter which can allow heterologous proteins to be expressed irrespective of glucose concentration according to cell growth, and is more potent than GAP, which is known as a strong constitutive promoter.

TABLE 2

Comparison between TEF Promoter and GAP Promoter Strengths in Fed-Batch Type Culture

|  | Glucose | | Glycerol | |
|---|---|---|---|---|
|  | Cell Concentration (A600) | Lipase Activity (U/ml) | Cell Concentration (A600) | Lipase Activity (U/ml) |
| *Pichia pastoris*/pTEF-AM-CLLip | 397 | 188 | 348 | 280 |
| *Pichia pastoris*/pGAP-AM-CLLip | 393 | 100 | 376 | 201 |

INDUSTRIAL APPLICABILITY

Having greater strength than GAP promoter and TEF promoters derived from other species, as described hitherto, the *Pichia pastoris*-derived TEF promoter of the present invention can be efficiently used for the production of heterologous proteins. Particularly, the promoter of the present invention is a constitutive promoter, and thus its activity is not affected by an inducer. Therefore, it can provide a solution to the problems occurring when an inducer is utilized during fermentation.

The invention claimed is:

1. An isolated promoter consisting of the nucleotide sequence of SEQ ID NO: 6.

2. A recombinant expression vector, comprising the promoter of claim 1 and a nucleotide sequence operably linked to the promoter coding for a heterologous protein.

3. An isolated host cell, transformed or transfected with the recombinant expression vector of claim 2.

4. The host cell according to claim 3, wherein the host cell is a yeast.

5. The host cell according to claim 4, wherein the yeast is *Pichia pastoris*.

6. A method for producing a heterologous protein, comprising culturing the host cell of claim 3 to express the heterologous protein, and isolating the heterologous protein.

7. A method for producing a heterologous protein, comprising culturing the host cell of claim 4 to express the heterologous protein, and isolating the heterologous protein.

8. A method for producing a heterologous protein, comprising culturing the host cell of claim 5 to express the heterologous protein, and isolating the heterologous protein.

* * * * *